United States Patent [19]

Bailey

[11] 4,249,009

[45] Feb. 3, 1981

[54] PROCESSES FOR PREPARING 2-CHLORO-5-TRIFLUOROMETHYLPYRIDINE

[75] Inventor: Thomas D. Bailey, Indianapolis, Ind.

[73] Assignee: Reilly Tar & Chemical Corp., Indianapolis, Ind.

[21] Appl. No.: 7,632

[22] Filed: Jan. 29, 1979

[51] Int. Cl.³ .......................................... C07D 213/26
[52] U.S. Cl. .................... 546/345; 546/298; 546/303
[58] Field of Search ............................... 546/303, 345

[56] References Cited

U.S. PATENT DOCUMENTS

| | | | |
|---|---|---|---|
| 3,609,158 | 9/1971 | Torba | 546/300 |
| 3,705,170 | 12/1972 | Torba | 546/302 |
| 4,038,396 | 7/1977 | Shen et al. | 546/114 |

*Primary Examiner*—Alan L. Rotman
*Attorney, Agent, or Firm*—Woodard, Weikart, Emhardt & Naughton

[57] ABSTRACT

One process comprises the step of reacting an amount of 5-carboxy-2-pyridone directly with both a suitable chlorinating agent and a suitable fluorinating agent to selectively transform both the 5-carboxy group and the 2-positioned oxygen function of the ring. A second process comprises the steps of reacting an amount of 5-carboxy-2-pyridone with a suitable fluorinating agent to selectively transform the 5-carboxy group without altering the 2-positioned oxygen function of the ring and reacting the 5-trifluoromethyl-2-pyridone thereby formed with a suitable chlorinating agent to cause 2-chloro-5-trifluoromethylpyridine to form. A third process comprises the steps of reacting an amount of a 5-carboxy-2-pyrone compound with a suitable fluorinating agent to selectively transform the 5-carboxy group without altering the 2-positioned oxygen function of the ring, reacting the 5-trifluoromethyl-2-pyrone compound thereby formed with an ammonia-containing agent in the presence of a caustic material to cause 5-trifluoromethyl-2-pyridone to form, and reacting the 5-trifluoromethyl-2-pyridone thereby formed with a suitable chlorinating agent to cause 2-chloro-5-trifluoromethylpyridine to form.

28 Claims, No Drawings

PROCESSES FOR PREPARING 2-CHLORO-5-TRIFLUOROMETHYLPYRIDINE

BACKGROUND OF THE INVENTION

This invention relates generally to plural-substituted pyridine derivatives and, particularly, to processes for preparing and isolating 2-chloro-5-trifluoromethylpyridine and using same.

Although a large number of functionally substituted pyridine compounds are known and capable of synthesis, certain patterns of disubstitution, in particular, on the pyridine ring are difficult to obtain by any convenient and commercially viable means. Pyridines having functional substituents in the 2- and 5- positions on the ring are often valuable derivatives, but fall within this category. For example, hydroxyl, cyano, carboxy, chloro and other groups are difficult to introduce into these positions on the pyridine ring.

One 2- and 5- disubstituted pyridine compound gaining in commercial interest in recent years is 2-chloro-5-trifluoromethylpyridine. It appears from the prior art that the compound would be useful as a plant growth regulator and useful for the suppression of nitrification of ammonia in the soil. Additional areas of use can be determined from U.S. Pat. Nos. 3,609,158 and 3,705,170. Still further, it has proven an important intermediate reaction product in the preparation of herbicides and for polymer modification.

Nevertheless, only three methods of synthesis for this pyridine compound have been reported, none of which have proven to be of particular commercial value. These known methods will be specifically described below following a background discussion of the synthesis reaction in general.

First, as to the trifluoromethyl substitution, it is generally known that alkyl and aromatic carboxylic acids react with sulfur tetrafluoride in the presence of hydrogen fluoride to give trifluoromethyl derivatives. Boswell et al., *Org. Reactions*, 21, 30 (1974). This reaction is known to take place in two steps as represented below.

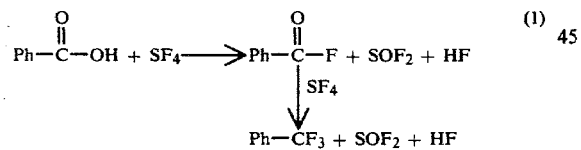

The first step is the facile conversion of the carboxylic acid to an acid fluoride which occurs at low temperatures. The second step is not as facile, but requires more vigorous conditions. The hydrofluoric acid both added and generated in the first step combine to act as a catalyst in the final trifluoromethyl formation. Although these steps are distinct, the reaction generally proceeds without isolation of the acid fluoride, with the initial reaction mixture simply being heated to convert the intermediate acid fluoride to the final trifluoromethyl group. Boswell et al., supra.

This trifluoromethylating reaction has been applied to various compounds including amino acids, simple pyridine carboxylic acids such as niacin and 3,5-dicarboxypyridine. Kobayashi et al., *Chem. Pharm. Bull.*, 15, 1896 (1967); Raasch, *J. Org. Chem.*, 27, 1406 (1962). It has also been applied to esters and anhydrides of these carboxylic acids to give the corresponding fluorinated ethers, the double-bonded oxygen functions being simply replaced during the fluorination reaction. Hasek, Smith, & Engelhardt, *J. Amer. Chem. Soc.*, 82, 543 (1960).

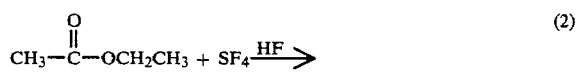

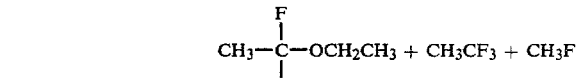

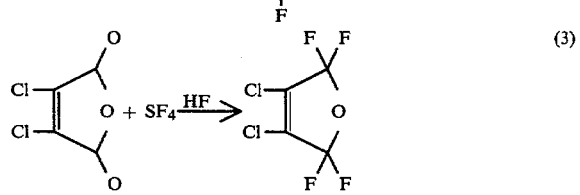

It is also known that this final trifluoromethylating step proceeds equally well when an acid chloride compound is used instead of the intermediate acid fluoride.

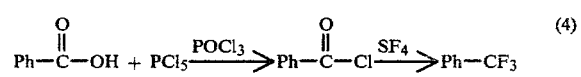

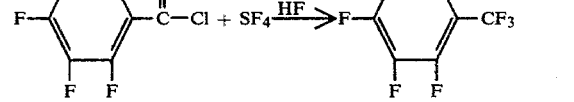

However, the reaction product is not always straightforward as in the following example where an unexpected chlorination resulted.

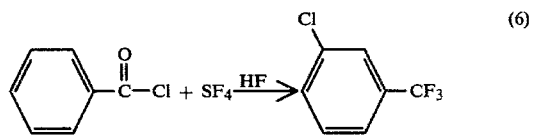

As to chlorine substitution in general, the standard method of acid chloride preparation is the reaction of a carboxylic acid with an agent such as phosphorus pentachloride, phosphorus oxychloride, or a combination of the two, or with a thionylchloride in the presence of a solvent such as dimethylformamide. J. March, *Advanced Organic Chemistry: Reactions, Mechanisms, and Structure*, 346-347 (1968).

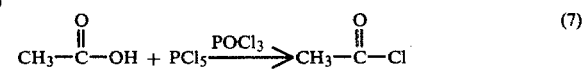

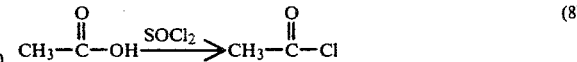

Similarly, 2- and 4-hydroxypyridines, also called pyridones, are known to readily convert to their 2- and 4-chlorine derivatives by reaction with these same reagents. Klingsburg, *Pyridine and Its Derivatives, Part Three*, 646 (1962). Abramovitch, *Pyridine and Its Derivatives*, 785, 790-791 (1974). 3-Hydroxypyridines are not affected by such reagents.

However, the presence of a hydroxy group is known to lead to undesirable reactions involving this additional oxygen function in the trifluoromethylation reaction. In particular, 2- and 4-hydroxypyridines have been shown to physically exist as a mixture of tautomeric forms, appearing both as the hydroxy and as the amide derivatives. R. Elderfield, *Heterocyclic Compounds,* 1, 435–440 (1950).

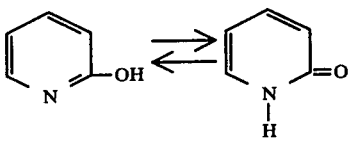
(9)

For this reason, these hydroxypyridines undergo reactions typical of both phenols and amides as also reported in the Elderfield reference.

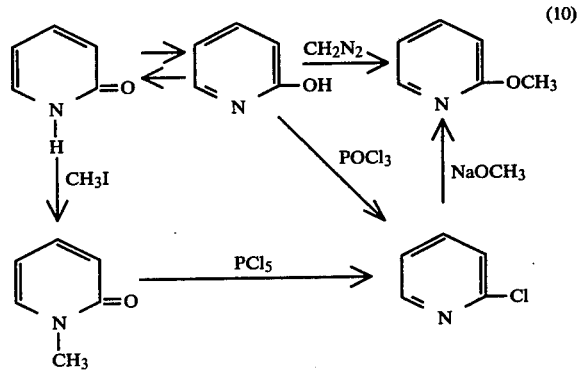
(10)

Similar behavior has been reported in substituted hydroxypyridines such as the 5-carboxy-2-hydroxypyridines, also known as 5-carboxy-2-pyridones in their alternate form. Klingsberg, *Pyridine and Its Derivatives, Part Three,* 646 (1962).

It is known that hydroxy groups give rise to fluoro groups by standard substitution upon treatment with sulfur tetrafluoride. Sharts & Sheppard, *Org. Reactions,* 21, 125 (1973). It is also known that amides react with sulfur tetrafluoride to give a variety of products. Hasel, Smith & Englehart, *J. Amer. Chem. Soc.,* 82, 543 (1966). For example, if the amide contains at least one nitrogen-hydrogen bond, cleavage at the nitrogen-carbon bond is reported to occur.

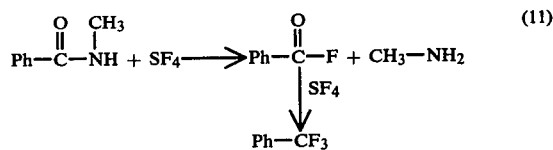
(11)

With this background, there are three reported methods for synthesis of this disubstituted 2-chloro-5-trifluoromethylpyridine.

The first reference is U.S. Pat. No. 2,516,402, issued on July 25, 1950 to McBee et al. This patent claims various new fluoromethylpyridines which were prepared by the chlorination of methylpyridines, in which complete substitution took place on the side-chain and to some extent on the ring as well. McBee et al. report that this chlorination on the pyridine ring, which is ordinarily difficult to accomplish, appears to be aided by the presence of one or more trichloromethyl groups on the ring. Fluorination of these side-chains was then accomplished with hydrogen fluoride.

A second reported synthesis is apparently disclosed in an abandoned U.S. Pat. application, Ser. No. 749,977 originally filed Aug. 5, 1968 and assigned to Dow Chemical Company of Midland, Michigan. The content of this abandoned application is not presently known, but it is believed to produce the trifluoromethyl-chloro derivative by standard halogen substitution from the trichloromethyl-chloro compound similar to the McBee et al. patent. This belief is based upon references in two later Dow patents, U.S. Pat. Nos. 3,705,170 and 3,609,158, to this abandoned application. Specifically, each patent cross-references this application and only generally discusses the preparation of its starting materials beginning at col. 20, l. 42 in Dow U.S. Pat. No. 3,705,170 and at col. 19, l. 49 in Dow U.S. Pat. No. 3,609,580.

A final synthesis of 2-chloro-5-trifluoromethylpyridine is reported in U.S. Pat. No. 4,038,396 issued to Shen et al. on July 26, 1977. The following series of reactions were disclosed in Example 111 of this patent beginning at column 23, line 62.

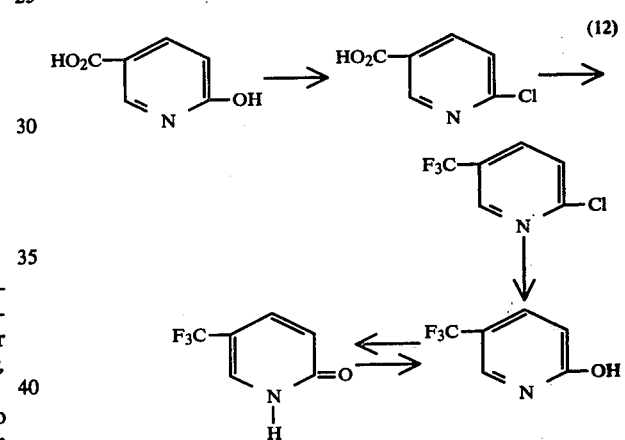
(12)

As seen in this representation, Shen et al. first teaches the chlorination of 6-hydroxynicotinic acid, also known as 5-carboxy-2-hydroxypyridine and 5-carboxy-2-pyridone, obtaining 2-chloro-5-carboxypyridine as the reaction product. As previously discussed, this chlorination actually involves two distinct steps, the acid chloride group being hydrolyzed back to the carboxylic acid when cooled in crushed ice prior to filtration. The 6-chloronicotinic acid intermediate is then subjected to standard trifluoromethylation using sulfur tetrafluoride in the presence of hydrogen fluoride also as previously described.

These three known methods are lengthy and complex, and are not known to be commercially significant. They further point to the need for the development of a viable, more efficient method for preparing this commercially valuable compound.

SUMMARY OF THE INVENTION

One aspect of this invention comprises several new processes for preparing 2-chloro-5-trifluoromethylpyridine.

One embodiment accomplishes this process by reacting an amount of 5-carboxy-2-pyridone, in either its hydroxy or amide form, directly with both a suitable chlorinating agent and suitable fluorinating agent in the absence of water to selectively transform the 5-carboxy group and the 2-positioned oxygen function of the ring. This direct one-step reaction is a significant improvement over the reported methods of synthesis, and particularly over the lengthy and more complex steps taught by the Shen et al. patent. Standard reaction conditions are observed and significant yields are achieved.

A second embodiment accomplishing this same process is an improvement of applicant's related discovery, as discussed below, in which nonisolated 5-trifluoromethyl-2-pyridone produced by applicant's new processes is further reacted with a suitable chlorinating agent to cause 2-chloro-5-trifluoromethylpyridine to form. This embodiment is also an advance over the art because of the unprecedented nature of applicant's companion discovery in addition to the simple, direct and efficient conversion of the intermediate compound to the desired chlorinated form.

DESCRIPTION OF THE PREFERRED EMBODIMENT

As indicated above, one aspect of this invention comprises several processes for preparing 2-chloro-5-trifluoromethylpyridines without the complexity or inefficiency of known methods. It is preferred that yields of the processes disclosed herein be at least 20% to be suitable for commercial applications. These processes are described in full below, with specific examples of each process following the detailed disclosure.

DIRECT PROCESS USING 5-CARBOXY-2-PYRIDONE

Defined broadly, this process comprises the single step of reacting an amount of 5-carboxy-2-pyridone directly with both a suitable chlorinating agent and suitable fluorinating agent in the absence of water to selectively transform the 5-carboxy group and the 2-positioned oxygen function of the ring.

In this context, reference to the substituted 2-pyridone compound is meant to include both the hydroxy and the amide tautomeric forms, as previously described. The term "suitable chlorinating agent" is meant to include any known or yet undiscovered chlorine-containing compound that is susceptible of chlorine substitution at a ring position. Examples of known agents include phosphorus pentachloride, phosphorus oxychloride, thionylchloride and the like. The term "suitable fluorinating agent" is likewise meant to include any known or yet undiscovered fluorine-containing compound that is susceptible of forming a trifluoromethyl group when reacted with a carboxy substituent. Examples of such agents include sulfur tetrafluoride, molybdenum hexafluoride and the like.

The idea of combining the chlorinating and the trifluoromethylating procedures into a single reaction with a carboxypyridone is not taught or suggested in the art. The prior art also does not teach or suggest the fluorinating or chlorinating, respectively, of a carboxypyridone which has been previously chlorinated or fluorinated, respectively, and not isolated from the reaction products of the earlier halogenation step. The potential advantages from this combination are several.

Trifluoromethylation of a monosubstituted carboxylic acid is known to require two distinct steps, as explained in the background section of this application. First, the carboxy group reacts with the selected agent, such as sulfur tetrafluoride, to produce an acid fluoride product. This intermediate then reacts a second time with sulfur tetrafluoride to form the final trifluoromethyl derivative.

It is also known that this trifluoromethylation proceeds equally well with preformed acid chlorides. Carboxylic acids are in turn known to convert to their acid chloride during standard chlorination procedures; but they are readily hydrolyzed back to their carboxy state in the presence of water.

Applicant has discovered that by reacting a carboxy- and hydroxy-containing compound with a mixture containing both a suitable chlorinating and a suitable fluorinating agent, both reactions proceed in an enhanced (synergistic) manner as seen in the following representation.

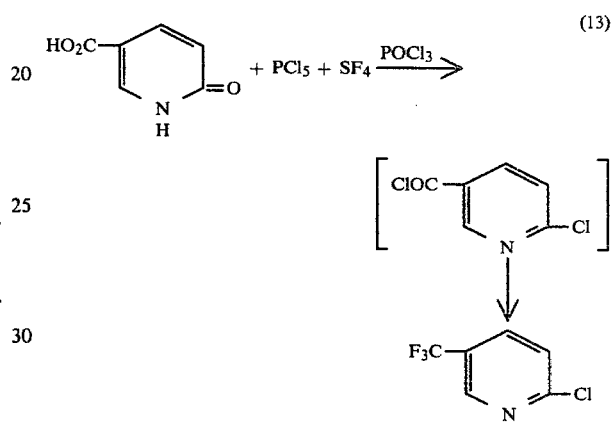

Specifically, the chlorination reaction is believed to proceed initially to produce an intermediate, nonisolated or discernable dichlorinated compound represented above in bracketed form. In this acid chloride state, trifluoromethylation proceeds directly without the need for the initial acid fluoride formation.

Applicant's discovery represents an important improvement over the art in that much less sulfur tetrafluoride, or other trifluoromethylating agent, is required to convert the carboxy acid to its trifluoromethyl form since the acid has been already converted to the acid chloride by the chlorinating agent. This in itself is a major economic improvement since sulfur tetrafluoride is very expensive relative to the phosphorus oxychloride-phosphorus pentachloride combination used for chlorination in the preferred process.

Furthermore, it is known that phosphorus pentafluoride is an effective catalyst for the conversion of carboxy acid to their trifluoromethyl forms when used with sulfur tetrafluoride. Chamberg, *Fluorine in Organic Chemistry*, 48–49 (1973). For this reason, and because of the generally known tendency of the halogen anion not to affect the catalytic qualities of a particular agent, the phosphorus pentachloride agent used in the chlorinating step of this process would be expected to perform a catalytic function in the final trifluoromethylation reaction.

Therefore, the phosphorus pentachloride plays the dual role of both chlorinating the compound and then acting as a catalyst for the trifluoromethyl conversion of the carboxy acid. This dual feature is untaught in the art, and experiments performed to date support this analysis.

The nonobviousness of this argument is further strengthened by comparison of the Shen et al. reference which specifically follows the more complex two-step chlorinating and trifluoromethylating procedure requiring the use of additional sulfur tetrafluoride and not taking advantage of the potential catalytic nature of the phosphorus pentachloride agent.

The preferred conditions for applicant's chlorination and trifluoromethylation reaction exhibit no significant variance from accepted procedures. These conditions are as follows:

An amount of 5-carboxy-2-pyridone was first placed in a reaction vessel. While the reaction vessel was one suitable for a batch process, the term as used herein is intended to encompass a reaction vessel suitable for a continuous process. Effective amounts of the suitable chlorinating agent and the suitable fluorinating agent were then placed therein. (No water was added to the reaction vessel.) In this context, these halogenating agents have been previously defined, and the term "effective amounts" is meant to define a sufficient quantity of the agents as determined by stoichiometric or past experimental means to permit the chlorination and trifluoromethylation reactions to proceed. The preferred agents are phosphorus oxychloride and phosphorous pentachloride, in combination, and sulfur tetrafluoride.

The vessel and its contents were then heated to a reaction temperature of between about 60° C. and 150° C. and were maintained at this elevated temperature for a period of between about 6 hours and about 24 hours. The precise temperature and period for the reaction depend, of course, upon many factors including available facilities, reagent concentrations, desired reaction yields and the like. As previously stated, an important consideration is that the reaction proceed without the addition of water in order that the acid chloride, once formed, is not significantly hydrolyzed before the trifluoromethylation occurs. With this in mind, experiments to data have shown the preferred temperature is 120° C. and the preferred reaction time is 15 hours to achieve a commercially satisfactory yield. It is desired for the compound to be isolated to achieve a purity of at least 60%, most preferrably at least 95%.

While the procedure disclosed illustrates the preferred method of having both the chlorinating and fluorinating agents present and available to react at the same time, an alternative procedure may be performed in a different way. This alternative procedure may be performed by running one halogenation reaction first and, without isolating the resultant products, thereafter running the second halogenation reaction.

Although not required, the reaction can proceed in the presence of a suitable solvent such as a chlorinated hydrocarbon, including chloroform, methylene chloride and the like.

Isolation of the 2-chloro-5-trifluoromethylpyridine product can then be accomplished by any convenient means. In the preferred method, the vessel is vented, the contents taken up in water, the pH adjusted to near neutral and the product isolated by extraction with chloroform.

Once isolated, this 2-chloro-5-trifluoromethylpyridine is useful as described above as a plant growth regulator and useful for the suppression of nitrification of ammonia in the soils. Still further, it has proven a valuable intermediate in the formation of various 2- and 5-disubstituted herbicides and for polymer modification.

INDIRECT PROCESS USING 5-CARBOXY-2-PYRIDONE

In this preferred process, the desired compound is finally prepared by reacting 5-trifluoromethyl-2-pyridone with a suitable chlorinating agent to cause 2-chloro-5-trifluoromethylpyridine to form. The conditions of the reaction are known and practiced in the art. Acceptable chlorinating agents include phosphorus pentachloride and phosphorus oxychloride, either alone or in combination, thionylchloride and the like. Although not necessary, a solvent such as dimethylformamide, chloroform or excess phosphorus oxychloride can also be added to the reaction if desired. A temperature range of between about 60° C. and about 150° C. and a reaction period of between about 4 hours and about 24 hours is proper; and experiments to date by applicant have shown the preferred reaction proceeds at 100° C. for a period of up to about 8 hours.

Isolation of the 2-chloro-5-trifluoromethylpyridine product is then accomplished by any convenient method. In the preferred process the unreacted, volatile phosphorus compounds are first removed by distillation, taking up the nonvolatile materials in water, and then neutralizing the solution with a caustic material before extracting the product into a suitable solvent. Examples of possible solvents include chlorinated hydrocarbons, ethers, aromatic hydrocarbons and water-immiscible alcohols. Specific examples in each class include chloroform, diethyl ether, toluene and 2-butanol. Suitable caustics that can be used include alkali hydroxides, ammonium hydroxide, alkali carbonates and the like, with sodium hydroxide being preferred.

The portion of this indirect process which chlorinates the 5-trifluoromethyl-2-pyridone is similar to the Klingsburg and Abramovitch references mentioned earlier. The indirect process as a whole is quite clearly distinguished from these or any other references by applicant's related discovery of a new process for preparing this intermediate 5-trifluoromethyl-2-pyridone compound. Specifically, applicant has discovered two new processes unexpected and unprecedented in the art, one of which includes a second intermediate compound also newly isolated and characterized by applicant's work. The two processes leading to the intermediate compound are represented below.

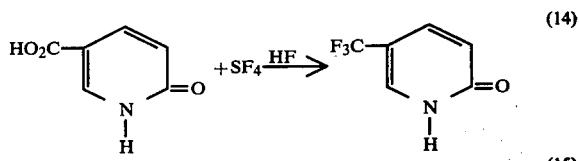

(14)

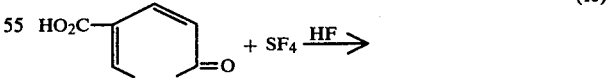

(15)

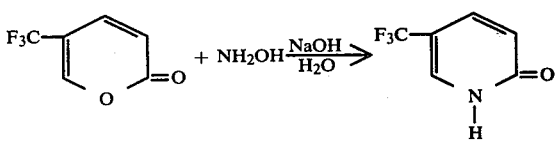

Reaction 14 involves the direct trifluoromethylation of the amide or hydroxy forms of 5-carboxy-2-pyridone to selectively replace the 5-carboxy group without fluorinating the 2-positioned oxygen function of the ring.

The preferred temperature range is between about 60° C. and 150° C., and the preferred period is between about 6 hours and about 24 hours. A catalytic amount of water or a suitable chlorinated hydrocarbon solvent can be used if desired, and isolation of the intermediate product is accomplished using known techniques.

Reaction 15 is a two-step procedure in which the initial trifluoromethylation of the 2-pyrone derivative is carried out under conditions identical to those of reaction 14. The new 5-trifluoromethyl-2-pyrone compound then reacts as normal pyrones in the presence of an ammonia-containing agent and water to give the corresponding 2-pyridone derivative.

These novel reactions to obtain the 5-trifluoromethyl-2-pyridone intermediate, or its 2-hydroxy form, are described in detail and accompanied by specific examples in applicant's companion patent application, U.S. Ser. No. 007,518, filed on Jan. 29, 1979 and entitled 5-TRIFLUOROMETHYL-2-PYRONE AND PROCESSES FOR MAKING SAME AND FOR MAKING 5-TRIFLUOROMETHYL-2-PYRIDONE. For this reason, this companion application is hereby expressly incorporated herein by reference as to all relevant and material disclosure therein.

The resultant preferred processes of this invention for the preparation of the commercially valuable 2-chloro-5-trifluoromethylpyridine compound are therefore represented as follows:

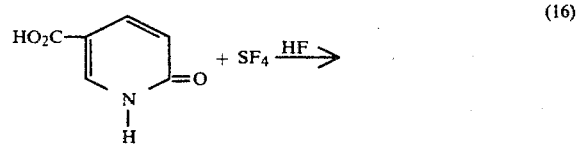

(16)

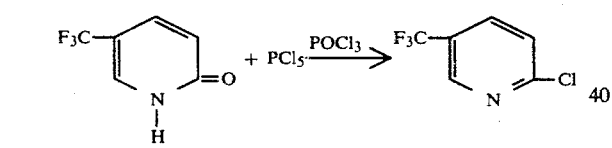

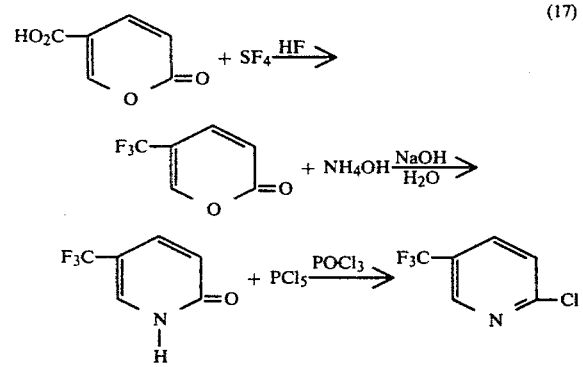

(17)

The success of these processes is unexpected in the art both for the reasons stated above and for the reasons contained in applicant's companion application, incorporated herein by reference.

In an effort to promote a better understanding of the principles of this invention, the following specific examples are presented to describe the preparation of specific compounds of the invention using the preferred processes already discussed. These examples are meant to be illustrative only and not restrictive or limiting of the scope of the invention, it being understood that only the preferred embodiments have been shown and described.

EXAMPLE 1

To a stainless steel pressure vessel was added 28 g of 2-hydroxy-5-carboxypyridine, 40 g phosphorus pentachloride and 40 g of sulfur tetrafluoride. The sealed vessel was heated to 120° C. for 18 hours, cooled to 25° C. and the volatile materials vented. The liquid contents of the vessel were slowly added to 200 cc of cold water and the pH adjusted to 7. The neutral solution was extracted three times with 100 cc of chloroform each time, the extracts dried over magnesium sulfate and the solvent removed by evaporation under reduced pressure to give 2-chloro-5-trifluoromethylpyridine. A yield in excess of 40% was achieved. This 2-chloro-5-trifluoromethylpyridine was found to reduce nitrification of ammonia in soil when formulated and applied in effective amounts as a spray or soil drench.

EXAMPLE 2

To a stainless steel pressure vessel was added 14 g of 2-hydroxy-5-carboxymethylpyridine, 27 g of thionyl chloride and 27 cc of sulfur tetrafluoride. The sealed vessel was heated to 125° C. for 14 hours and thereafter cooled to room temperature. By venting the vessel and isolating the compound as in Example 1, 2-chloro-5-trifluoromethylpyridine is obtained. This 2-chloro-5-trifluoromethylpyridine was applied to selected pig weed plants and found to effect a change in the growth rate pattern of the plant.

EXAMPLE 3

The reaction as in Example 1 was carried out using phosphorus pentachloride, phosphorus oxychloride and sulfur tetrafluoride to give 2-chloro-5-trifluoromethylpyridine.

EXAMPLE 4

To a stainless steel pressure vessel is added 22 g of 2-hydroxy-5-carboxypyridine, 2.2 g of water and 20 cc of sulfur tetrafluoride. The sealed vessel was heated to 140° C. for 10 hours and cooled to 25° C. and vented. The liquid contents were dissolved in 200 cc of water, the pH adjusted to 7.1 with sodium carbonate and the neutral solution extracted with chloroform to give 2-hydroxy-5-trifluoromethylpyridine upon evaporation. 5 g of this 2-hydroxy-5-trifluoromethylpyridine was added to 25 g of phosphorus pentachloride and heated for 120° C. for 6 hours. The cooled reaction mixture was added slowly to 200 cc of water and the pH adjusted to 5.5 with sodium carbonate. The solution was extracted three times with 100 cc of chloroform each time to give on evaporation 2-chloro-5-trifluoromethylpyridine.

EXAMPLE 5

To 10 g of 2-hydroxy-5-trifluoromethylpyridine obtained as in Example 1 was added 20 cc of dimethylformamide and 30 g of phosphorus oxychloride. The resulting solution was heated to 140° C. for 3 hours, cooled to room temperature and slowly diluted with 200 cc of cold water. The acid solution was slowly neutralized with sodium carbonate and extracted three times with 200 cc of pentane. The pentane was removed by evaporation to give 2-chloro-5-trifluoromethylpyridine as a yellow oil.

EXAMPLE 6

30 g of thionyl chloride was added to 12 g of 2-hydroxy-5-trifluoromethylpyridine dissolved in 20 g of dimethylformamide. The 2-hydroxy-5-trifluoromethylpyridine was prepared as disclosed in Examples 4 and 5 of applicant's copending application earlier referred to and incorporated herein by reference. The solution was then heated to 60° C. for 24 hours, cooled to 20° C. and diluted with 200 cc of water and the pH adjusted to 5.5 with sodium carbonate. The acid solution was extracted three times with 100 cc of chloroform each time and the extracts washed three times with 20 cc of water each time. The chloroform solution was evaporated at reduced pressure to give 2-chloro-5-trifluoromethylpyridine.

EXAMPLE 7

The reaction as in Example 1 was carried out using a mixture of phosphorus oxychloride and phosphorus pentachloride in combination as the chlorinating agent to give 2-chloro-5-trifluoromethylpyridine.

EXAMPLE 8

To a stainless steel presure vessel was added 32 g of 2-hydroxy-5-carboxypyridine and 54 g phosphorus pentachloride. The sealed vessel was heated to 120° C. for 6 hours, cooled to 25° C. and vented of the volatile materials. After cooling, 44 g of sulfur tetrafluoride were added to the contents and the sealed vessel was heated to 120° C. for 8 hours, cooled to 25° C. and vented of the volatile materials. The liquid contents of the vessel were slowly added to 200 cc of cold water and the pH adjusted to 7. The neutral solution was extracted three times with 100 cc of chloroform each time, the extracts dried over magnesium sulfate and the solvent removed by evaporation under reduced pressure to give 2-chloro-5-trifluoromethylpyridine.

What is claimed is:

1. A process for preparing 2-chloro-5-trifluoromethylpyridine comprising the step of reacting an amount of 5-carboxy-2-pyridone directly with both a suitable chlorinating agent and a suitable fluorinating agent to selectively transform both the 2-position oxygen function of the ring and the 5-carboxy group, respectively.

2. The process in claim 1 wherein said reacting is at a temperature of between about 60° C. and about 150° C.

3. The process in claim 2 wherein said reacting is for a period of between about 6 hours and about 24 hours.

4. The process in claim 1 or 2 wherein said reacting is in the presence of a chlorinated hydrocarbon solvent.

5. The process in claim 1 or 2 wherein the chlorinating agent is a mixture of phosphorus oxychloride and phosphorus pentachloride and the fluorinating agent is sulfur tetrafluoride.

6. The process in claim 5 wherein said reacting is at a temperature of about 120° C. and for a period of about 15 hours.

7. The process of claim 1 which additionally includes the step of isolating the desired 2-chloro-5-trifluoromethylpyridine to achieve a purity of at least 60%.

8. A process for preparing 2-chloro-5-trifluoromethylpyridine, comprising the steps of:
   (a) reacting an amount of 5-carboxy-2-pyridone with a suitable fluorinating agent to selectively transform the 5-carboxy group without altering the 2-positioned oxygen function of the ring; and
   (b) reacting the 5-trifluoromethyl-2-pyridone thereby formed with a suitable chlorinating agent to cause 2-chloro-5-trifluoromethylpyridine to form.

9. The process in claim 8 wherein said reacting steps are at a temperature of between about 60° C. and about 150° C.

10. The process in claim 9 wherein said reacting steps are for a period of between about 6 hours and about 24 hours.

11. The process in claim 8 or 9 wherein said reacting steps are in the presence of a chlorinated hydrocarbon solvent.

12. The process in claim 8 or 9 wherein the chlorinating agent is a mixture of phosphorus oxychloride and phosphorus pentachloride and the fluorinating agent is sulfur tetrafluoride.

13. The process in claim 12 wherein said reacting steps are at a temperature of about 120° C. and for a period of about 15 hours.

14. The process of claim 8 which additionally includes the step of isolating the desired 2-chloro-5-trifluoromethylpyridine to achieve a purity of at least 60%.

15. A process for preparing 2-chloro-5-trifluoromethylpyridine, comprising the steps of:
   (a) reacting an amount of a 5-carboxy-2-pyrone compound with a suitable fluorinating agent to selectively transform the 5-carboxy group without altering the 2-positioned oxygen function of the ring;
   (b) reacting the 5-trifluoromethyl-2-pyrone compound thereby formed with an ammonia-containing agent in the presence of water and a caustic material to cause 5-trifluoromethyl-2-pyridone to form;
   (c) removing water remaining after said reacting of step b; and
   (d) after said removing, reacting the 5-trifluoromethyl-2-pyridone formed in step b with a suitable chlorinating agent to cause 2-chloro-5-trifluoromethylpyridine to form.

16. The process in claim 15 wherein said reacting steps are at a temperature of between about 60° C. and about 150° C.

17. The process in claim 16 wherein said reacting steps are for a period of between about 6 hours and about 24 hours.

18. The process in claim 16 or 17 wherein said reacting steps are in the presence of a chlorinated hydrocarbon solvent.

19. The process in claim 16 or 17 wherein the chlorinating agent is a mixture of phosphorus oxychloride and phosphorus pentachloride and the fluorinating agent is sulfur tetrafluoride.

20. The process in claim 19 wherein said reacting steps are at a temperature of about 120° C. and for a period of about 15 hours.

21. The process of claim 15 which additionally includes the step of isolating the desired 2-chloro-5-trifluoromethylpyridine to achieve a purity of at least 60%.

22. A process for preparing 2-chloro-5-trifluoromethylpyridine, comprising the steps of:
   (a) placing an amount of 5-carboxy-2-pyridone in a reaction vessel,
   (b) placing an amount of a suitable chlorinating agent in said reaction vessel,
   (c) placing an amount of a suitable fluorinating agent in said reaction vessel, and (d) after steps a, b and c, and without removing the contents placed in steps a, b and c, bringing the contents of said reaction vessel to a temperature sufficient for halogenation to occur.

23. The process of claim 22 which additionally includes the step of
   (e) after said bringing, isolating the desired 2-chloro-5-trifluoromethylpyridine.

24. The process of claim 23 in which said isolating achieves a purity of at least 60%.

25. The process of claim 24 in which said isolating achieves a purity of at least 95%.

26. The process of claim 22 in which said bringing is accomplished for such a time to achieve a yield of at least 20%.

27. The process of claim 22 which additionally includes the step of bringing the contents of said reaction vessel to a temperature sufficient for halogenation to occur after steps a and b and before step c.

28. The process of claim 22 in which steps a, b, and c are each performed before the contents of said reaction vessel are brought to a temperature sufficient for halogenation to occur.

* * * * *